(12) United States Patent
Hoshino

(10) Patent No.: US 12,133,921 B2
(45) Date of Patent: Nov. 5, 2024

(54) CAPSULE FILLING COMPOSITION, METHOD OF PRODUCING CAPSULE FORMULATION WITH THE USE OF CAPSULE FILLING COMPOSITION, AND CAPSULE FORMULATION

(71) Applicant: SHIN-ETSU CHEMICAL CO., LTD., Tokyo (JP)

(72) Inventor: Takafumi Hoshino, Yokohama (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 17/082,042

(22) Filed: Oct. 28, 2020

(65) Prior Publication Data

US 2021/0121409 A1    Apr. 29, 2021

(30) Foreign Application Priority Data

Oct. 29, 2019 (JP) ................. 2019-196189

(51) Int. Cl.
*A61K 9/48* (2006.01)
*A61J 3/07* (2006.01)
*A61K 47/38* (2006.01)

(52) U.S. Cl.
CPC ............ *A61K 9/4833* (2013.01); *A61J 3/074* (2013.01); *A61K 9/4808* (2013.01); *A61K 9/4866* (2013.01); *A61K 47/38* (2013.01)

(58) Field of Classification Search
CPC ............... A61K 9/4833; A61K 9/4808; A61K 9/4866; A61K 47/38; A61J 3/074
See application file for complete search history.

(56) References Cited

U.S. PATENT DOCUMENTS

| | | | | |
|---|---|---|---|---|
| 4,294,829 A * | 10/1981 | Suzuki | ........... | A61K 9/0043 514/420 |
| 4,884,602 A | 12/1989 | Yamamoto | | |
| 5,059,587 A | 10/1991 | Yamamoto | | |
| 9,616,036 B2 * | 4/2017 | Brackhagen | ......... | A61K 9/2054 |
| 2002/0042393 A1 | 4/2002 | Oobae | | |
| 2011/0062630 A1 * | 3/2011 | Honda | ........... | A61K 9/2054 264/299 |
| 2015/0065548 A1 * | 3/2015 | Adden | ........... | C09D 101/28 514/391 |

FOREIGN PATENT DOCUMENTS

| | | |
|---|---|---|
| CN | 104758180 A | 7/2015 |
| EP | 3354283 | 8/2018 |
| JP | 2009114113 | 5/2009 |
| JP | 5324302 | 10/2013 |
| JP | 2018199631 | 12/2018 |
| WO | 85/004100 | 9/1985 |
| WO | 2013/154390 | 10/2013 |

OTHER PUBLICATIONS

Japan Society of Pharmaceutical Machinery and Engineering (ed.), "Handbook of pharmaceutical machinery and engineering, second edition", pp. 299-300, 2010.
Ghori, Muhammad U., and Barbara R. Conway. "Powder compaction: Compression properties of cellulose ethers." British Journal of Pharmacy 1.1 (2016): 19.
T L Rogers "Hypromellose" In handbook of pharmaceuticals Excipients, Feb. 20, 2009, Pharmaceutical Press, UK, pp. 326-329.
Rowe, Raymond C., et al. Handbook of pharmaceutical excipients, Hydroxypropyl Cellulose, Low-Substituted, Jan. 1, 2006, Handbook of Pharmaceutical Excipients, Pharmaceutical Press London, pp. 341-343.
Armstrong, N. Anthony. "The instrumentation of capsule-filling machinery." Tablet and capsule machine instrumentation (2008): 207.
Extended European Search Report of corresponding EP patent application No. 20204631.8, Date of Drafting: Mar. 23, 2021.
EPO_Communication pursuant to EPC Art. 94(3) for corresponding European Patent Application No. Application No. EP 20204631.8, Sep. 5, 2022.
Chinese Office action (English machine translation of Office Action), Patent Application No. 202011171746.0 Date of Drafting: Aug. 3, 2023.
EPO Communication pursuant to Art. 115(1) from EPO, Patent Application No. 20204631.8, Date of Drafting: Dec. 14, 2023.
Younes et al. "Safety of low-substituted hydroxypropyl cellulose (L-HPC) to be used as a food additive in food supplements in tablet form," EFSA Journal 2018; 16(1):5062.
Office Action from JPO (English machine translation of Office Action), Patent Application No. JP2020-180288 Date of Drafting: Nov. 21, 2023.
European Patent Office, "Provision of the minutes in accordance with Rule 124(4) EPC" for Patent Application No. 20204631.8, pp. 1-9, Date of Issuance Jun. 4, 2024, Netherlands.
Wei Ming Pharmaceutical Extract, "L-HPC (Low-Substituted hydroxypropylcellulose)", pp. 1-9, Date of Publication: May 17, 2024 (URL: https://weimingpharma.bitdocs.ai/share/e/v86CxhlhYGqZPrjp).
Sidley Chemical CO., LTD. Extract, Hydroxypropyl Cellulose H-Hpc/L-Hpc, pp. 1-7, Date of Publication: May 17, 2024 (URL: https://sidleychem2019.en.made-in-china.com/product/DTBpNoLvnQWX/China-Hydroxypropyl-Cellulose-Hpc-L-Hpc-H.html).

(Continued)

*Primary Examiner* — Robert A Wax
*Assistant Examiner* — Olga V. Tcherkasskaya
(74) *Attorney, Agent, or Firm* — J M B Davis Ben-David

(57) ABSTRACT

The objective of the present invention is to provide a capsule filling composition which can stably produce a capsule formulation by suppressing the flow of components out of the capsule body during capsule filling, regardless of the compressibility of an active ingredient such as drugs and health foods, so that a favorable capsule filling can be achieved; and a method of producing a capsule formulation with the use of such a capsule filling composition, as well as a capsule formulation. The objective is achieved by a method of producing a capsule formulation, comprising subjecting a capsule filling composition containing an active ingredient and a cellulose ether powder to a funnel system powder filling or a die-compression system powder filling to obtain the capsule formulation, and the like.

6 Claims, No Drawings

(56) References Cited

OTHER PUBLICATIONS

China National Intellectual Property Administration, Chinese Office action for Patent Application No. 202011171746.0, pp. 1-7, Date of Issuance: May 13, 2024, PRC.
Japanese Patent Office, Decision of Refusal for Patent Application No. JP2020-180288, pp. 1-8, Date of Issuance: Jun. 25, 2024, Japan.
Intellectual Property India, First Examination Report for Patent Application No. 202044047007, pp. 1-6, Date of Issuance: Aug. 12, 2024, India.

* cited by examiner

CAPSULE FILLING COMPOSITION, METHOD OF PRODUCING CAPSULE FORMULATION WITH THE USE OF CAPSULE FILLING COMPOSITION, AND CAPSULE FORMULATION

CROSS-REFERENCE TO RELATED APPLICATION

Benefit is claimed to Japanese Patent Application No. JP2019-196189, filed on Oct. 29, 2019, the contents of which are incorporated by reference herein in their entirety.

TECHNICAL FIELD

The present invention relates to a capsule filling composition which can be used to fill a capsule, and a method of producing a capsule formulation with the use of such a capsule filling composition, as well as a capsule formulation.

BACKGROUND ART

In the fields of pharmaceuticals and foods, capsule formulations in which components such as drugs and health foods is filled in a capsule container are produced by automatically filling the components such as drugs and health foods into a hard capsule using a capsule filling machine. Typically, capsule filling machines are constructed such that the continuous and automatic production of capsule formulations can be achieved by separating an empty hard capsule, in which a cap and a body supplied have been temporarily coupled together, into a cap and a body; filling a constant weight of components into the body; and then coupling the cap and the body together again.

In Non-Patent Document 1, there is described seven methods consisting of auger system powder filling, die-compression system powder filling, funnel system powder filling, vibration system powder filling, granule filling, tablet filling and liquid drug filling as a method of filling components. Among them, the die-compression system powder filling accords to the following method: compressing, with a tapping rod, powders introduced into a molding plate, scraping off excess powders off, and then transferring the compressed powder to a capsule body. The funnel system powder filling accords to the following method: pushing a funnel for capsule filling into a powder layer to compress powders, and then transferring the compressed powders to a capsule body.

Both of the die-compression system powder filling and the funnel system powder filling include adding and mixing additive agents such as diluting agent to components such as drugs and health foods to obtain homogenous powders or granules obtained by granulating such a homogenous powder in a suitable method, and then lightly compression and filling the powders or the granules.

SUMMARY OF THE INVENTION

Problems to be Solved by the Invention

However, the components to be filled into a capsule cover a wide variety of drugs and health foods so that compression may not be sufficiently achieved in some types of the components. As a result, this leads to problems in which, for example, weight variations are caused by flowing components such as drugs and health foods out of a capsule body due to mechanical vibrations during capsule filling, thereby failing to produce capsule formulations having a constant weight. Actually, since there are many drugs and health foods with poor compressibility, it is probable to fail to stably filling such drugs and health foods with a predetermined amount into a capsule.

In view of the above circumstances, it is an objective of the present invention to provide a capsule filling composition which can stably produce a capsule formulation by suppressing the flow of components out of the capsule body during capsule filling, regardless of the compressibility of an active ingredient such as drugs and health foods, so that a favorable capsule filling can be achieved; and a method of producing a capsule formulation with the use of such a capsule filling composition, as well as a capsule formulation.

Means of Solving the Problems

In the course of extensive efforts to find a way to solve the above-identified problems, the present inventor has surprisingly found that a composition which contains as components a cellulose ether powder together with an active ingredient is excellent in compressibility, and can suppress the flow of components out of a capsule body during capsule filling. By using such a composition, it is possible to suppress weight variations for each capsule formulation based on capsule filling, and to stably produce capsule formulations having a constant weight.

Finally, on the basis of the above findings, the inventor has successfully invented a method of producing a capsule formulation at least including subjecting a capsule filling composition comprising an active ingredient and a cellulose ether powder to a funnel system powder filling or a die-compression system powder filling to prepare a compressed product, and filling a capsule container with the compressed product to obtain the capsule formulation; a capsule filling composition containing an active ingredient and a cellulose ether powder; and a capsule formulation containing such a capsule filling composition, as a possible solution to achieve the objective of the present invention. Such as, the present invention has been completed on the basis of the findings and successful examples that were first found or obtained by the present inventor.

According to the present invention, there is provided a capsule filling composition, a method of producing a capsule formulation, and a capsule formulation in the following aspects:

[1] a method of producing a capsule formulation, including subjecting a capsule filling composition containing an active ingredient and a cellulose ether powder to a funnel system powder filling or a die-compression system powder filling to prepare a compressed product; and filling the compressed product into a capsule container to obtain the capsule formulation;

[2] the method according to [1] above, wherein the cellulose ether powder is a cellulose ether powder having an average particle size equal to or less than 150 μm;

[3] the method according to [1] or [2] above, wherein the cellulose ether powder is a cellulose ether powder having a loose bulk density equal to or less than 0.55 g/mL;

[4] the method according to any one of [1] to [3] above, further including dry blending a raw material containing an active ingredient and a cellulose ether powder to obtain a capsule filling composition containing the active ingredient and the cellulose ether powder;

[5] the method according to any one of [1] to [4] above, wherein the cellulose ether powder is at least one cellulose ether powder selected from the group consisting of nonionic water-soluble cellulose ether, ionic water-soluble cellulose ether and salt thereof, nonionic water-insoluble cellulose ether, and esterified cellulose ether;

[6] the method according to [5] above, wherein the nonionic water-soluble cellulose ether is at least one nonionic water-soluble cellulose ether selected from the group consisting of nonionic water-soluble alkyl cellulose, nonionic water-soluble hydroxyalkyl cellulose and nonionic water-soluble hydroxyalkylalkyl cellulose;

[7] a capsule filling composition, containing an active ingredient and a cellulose ether powder;

[8] the composition according to [7] above, wherein the cellulose ether powder is a cellulose ether powder having an average particle size equal to or less than 150 μm;

[9] the composition according to [7] or [8] above, wherein the cellulose ether powder is a cellulose ether powder having a loose bulk density equal to or less than 0.55 g/mL;

[10] the composition according to any one of [7] to [9], wherein the cellulose ether powder is at least one cellulose ether powder selected from the group consisting of nonionic water-soluble cellulose ether, ionic water-soluble cellulose ether and salt thereof, nonionic water-insoluble cellulose ether, and esterified cellulose ether;

[11] the composition according to [10], wherein the nonionic water-soluble cellulose ether is at least one nonionic water-soluble cellulose ether selected from the group consisting of nonionic water-soluble alkyl cellulose, nonionic water-soluble hydroxyalkyl cellulose and nonionic water-soluble hydroxyalkylalkyl cellulose; and

[12] a capsule formulation, containing the composition according to any one of [7] to [11] above.

Effect of the Invention

According to the present invention, in the step of producing a capsule formulation, the outflow of components such as drugs and health foods from the inside of capsule body during capsule filling can be suppressed. According to the present invention, it is expected that favorable capsule filling allows weight variation for capsule formulations to be suppressed so that capsule formulations containing components with a constant weight can be stably produced.

DESCRIPTION OF EMBODIMENTS

While a capsule filling composition, a method of producing a capsule formulation and a capsule formulation that form one embodiment of the present invention will now be described in detail, the present invention may take various embodiments to the extent that its objective can be achieved.

Unless otherwise specified, each term used herein is used in the meaning commonly used by those skilled in the art and should not be construed to have any meaning that is unduly limiting. Also, any speculations and theories herein are made on the basis of the knowledge and experiences of the present inventors and as such, the present invention is not bound by any such speculations and theories.

While the term "composition" is not particularly limited and means composition as well known, it is, for example, comprised of combination of two or more components. The term "raw material" means one component or combination of two or more components to form a composition.

The term "and/or" as used herein means either any one of, any combination of two or more of, or combination of all of listed related items.

The term "content" as used herein is equivalent to "concentration" and means the proportion of a component relative to the total amount of a composition containing the component. Unless otherwise specified, the unit of content herein indicates % by mass or "wt %." It should be noted, however, that the total amount of the contents of components do not exceed 100 wt %.

The wording "to" for indicating a range of values is intended to include values preceding and following the wording; for example, "0 wt % to 100 wt %" means a range from 0 wt % or more and 100 wt % or less.

The terms "include," "comprise," and "contain" mean that an element (s) other than an element (s) as explicitly indicated can be added as inclusions, which are, for example, synonymous with "at least include," but encompasses the meaning of "consist of" and "substantially consist of". In other words, the terms may mean, for example, to include an element (s) as explicitly indicated as well as any one element or any two or more elements, to consist of an element (s) as explicitly indicated, or substantially consist of an element (s) as explicitly indicated. Such elements include limitations such as components, steps, conditions, and parameters.

The number of digits of an integer equals to its significant figure. For example, 1 has one significant figure and 10 has two significant figures. For a decimal number, the number of digits after a decimal point equals to its significant figure. For example, 0.1 has one significant figure and 0.10 has two significant figures.

<Capsule Filling Composition>

The capsule filling composition according to one embodiment of the present invention includes an active ingredient and a cellulose ether powder.

The active ingredient is not particularly limited as long as it is an orally administrable active ingredient. The active ingredient includes, for example, drugs used in pharmaceutical products, as well as active ingredients used in health foods such as foods with nutrient function claims, foods for specified health use, and foods with function claims.

Examples of the drugs used in pharmaceutical products include central nervous system drugs, circulatory system drugs, respiratory system drugs, digestive system drugs, antibiotics, antitussive/expectorant agents, antihistamine agents, antipyretic analgesic/antiinflammatory agents, diuretic agents, autonomic nerve agents, antimalarial agents, antidiarrheal drugs, psychotropic agents, vitamins, derivatives thereof and the like.

Examples of the central nervous system drugs include diazepam, idebenone, naproxen, piroxicam, indomethacin, sulindac, lorazepam, nitrazepam, phenytoin, acetaminophen, ethenzamide, ketoprofen, chlordiazepoxide and the like.

Examples of the circulatory system drugs include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, alprenolol hydrochloride and the like.

Examples of the respiratory system drugs include amlexanox, dextromethorphan, theophylline, pseudoephedrine, salbutamol, guaifenesin and the like.

Examples of the digestive system drugs include benzimidazole type drugs having antiulcer activity such as 2-[[3-methyl-4-(2,2,2-trifluoroethoxy)-2-pyridyl]methylsulfinyl] benzimidazole and 5-methoxy-2-[(4-methoxy-3,5-dimethyl-2-pyridyl)methylsulfinyl]benzimidazole; cimetidine, ranitidine, pirenzepine hydrochloride, pancreatin, bisacodyl, 5-aminosalicylic acid and the like.

Examples of the antibiotics include talampicillin hydrochloride, bacampicillin hydrochloride, cefaclor, erythromycin and the like. Examples of the antitussive/expectorant agents include noscapine hydrochloride, carbetapentane citrate, isoaminile citrate, dimemorfan phosphate and the like.

Examples of the antihistamine agents include chlorpheniramine maleate, diphenhydramine hydrochloride, promethazine hydrochloride and the like. Examples of the antipyretic analgesic/antiinflammatory agents include ibuprofen, diclofenac sodium, flufenamic acid, sulpyrine, aspirin, ketoprofen and the like.

Examples of the diuretic agents include caffeine and the like. Examples of the autonomic nerve agents include dihydrocodeine phosphate, dl-methylephedrine hydrochloride, atropine sulfate, acetylcholine chloride, neostigmine and the like.

Examples of the antimalarial agents include quinine hydrochloride and the like. Examples of the antidiarrheal drugs include loperamide hydrochloride and the like. Examples of the psychotropic agents include chlorpromazine and the like.

Examples of the vitamins and derivatives thereof include vitamin A, vitamin $B_1$, fursultiamine, vitamin $B_2$, vitamin $B_6$, vitamin $B_{12}$, vitamin C, vitamin D, vitamin E, vitamin K, calcium pantothenate, tranexamic acid and the like.

Examples of the active ingredients used in health foods include the vitamins and derivatives thereof, minerals, carotenoids, amino acids and derivatives thereof, plant extracts, health food materials and the like.

Examples of the minerals include calcium, magnesium, manganese, zinc, iron, copper, selenium, chromium, sulfur, iodine and the like.

Examples of the carotenoids include β-carotene, α-carotene, lutein, cryptoxanthin, zeaxanthin, lycopene, astaxanthin, multi-carotene and the like.

Examples of the amino acids include acidic amino acids, basic amino acids, neutral amino acids, acidic amino acid amides and the like. Examples of the acidic amino acids include aspartic acid, glutamic acid and the like. Examples of the basic amino acids include lysine, arginine, histidine and the like.

Examples of the neutral amino acids include linear aliphatic amino acids such as alanine and glycine; branched aliphatic amino acids such as valine, leucine and isoleucine; hydroxy amino acids such as serine and threonine; sulfur-containing amino acids such as cysteine and methionine; aromatic amino acids such as phenylalanine and tyrosine; heterocyclic amino acids such as tryptophan; imino acids such as proline; and the like.

Examples of the acidic amino acid amides include asparagine, glutamine and the like. Examples of the amino acid derivatives include acetylglutamine, acetylcysteine, carboxymethylcysteine, acetyltyrosine, acetylhydroxyproline, 5-hydroxyproline, glutathione, creatine, S-adenosylmethionine, glycylglycine, glycylglutamine, dopa, alanylglutamine, carnitine, γ-aminobutyric acid and the like.

Examples of the plant extracts include aloe, propolis, agarix, ginseng, *Ginkgo biloba*, turmeric, curcumin, germinated brown rice, shiitake mushroom mycelium, beetle tea, sweet tea, fomes yucatensis, sesame, garlic, maca, chinese caterpillar fungus, chamomile, capsicum and the like.

Examples of the health food materials include royal jelly, dietary fiber, protein, bifidobacteria, lactic acid bacteria, chitosan, yeast, koji (rice malt), glucosamine, lecithin, polyphenol, animal fish cartilage, softshell turtle, lactoferrin, Shijimi (Corbicula), eicosapentaenoic acid, germanium, enzyme, creatine, carnitine, citric acid, raspberry ketone, coenzyme Q10, methylsulfonylmethane, phospholipid-binding soybean peptide and the like.

The active ingredient may be used either individually or in combination of two or more of the above-mentioned active ingredients. The active ingredient may be commercially available or may be produced by known methods. While the form of the active ingredient is not particularly limited, the active ingredient is preferably in the form of solid such as powder in consideration of favorable mixability with a cellulose ether powder. When the active ingredient is in the form of liquid, the active ingredient is preferably processed into the form of solid for use by using a carrier, for example, in the form of powder.

The active ingredient is not particularly limited in terms of compressibility. The active ingredient used may be excellent or inferior in compressibility. In this regard, the capsule filling composition according to one embodiment of the present invention contains the cellulose ether powder together with the active ingredient so that the capsule filling composition is excellent in compressibility. As a result, the capsule filling composition has the advantage that any active ingredients inferior in compressibility can be used.

The compressibility of the active ingredient may be evaluated by compressibility index. The compressibility index of the active ingredient is preferably equal to or more than 3%, more preferably 5% to 100%, in terms of stable production of capsule formulations. The compressibility index of the active ingredient is a value determined according to the method as described in Examples below.

While the content of the active ingredient in the capsule filling composition is not particularly limited, the content is preferably in the range between 0.5 wt % and 99.5 wt %, more preferably between 0.75 wt % and 99.0 wt %, and still more preferably between 1 wt % and 95 wt %.

The capsule filling composition according to one embodiment of the present invention includes the cellulose ether powder together with the active ingredient. In the capsule filling composition, the cellulose ether powder serves as a binder and contributes to compressibility of compressed product.

The cellulose ether powder is not particularly limited in terms of property as long as the cellulose ether powder can improve compressibility of the capsule filling composition.

As described in Examples below, the smaller the average particle size of the cellulose ether powder is, the better compressibility the capsule filling composition is. Therefore, in terms of compressibility, the average particle size of the cellulose ether powder is preferably equal to or less than 150 μm, more preferably in the range between 1 μm and 100 μm, and still more preferably between 5 μm and 80 μm. The average particle size of the cellulose ether powder is a value determined by the method as described in Examples below (50% cumulative value of volume-based cumulative particle size distribution curve according to dry laser diffraction method).

In terms of compressibility, the loose bulk density of cellulose ether powder is preferably equal to or less than 0.55 g/mL, more preferably in the range between 0.05 g/mL and 0.45 g/mL, and still more preferably between 0.05 g/mL and 0.35 g/mL. The loose bulk density of cellulose ether powder is a value determined by the method as described in Examples below.

The cellulose ether powder includes nonionic water-soluble cellulose ether, ionic water-soluble cellulose ether and salt thereof, nonionic water-insoluble cellulose ether, esterified cellulose ether and the like.

The nonionic water-soluble cellulose ether includes nonionic water-soluble alkyl cellulose, nonionic water-soluble hydroxyalkyl cellulose, nonionic water-soluble hydroxyalkylalkyl cellulose and the like.

While the nonionic water-soluble alkyl cellulose is not particularly limited, it includes methylcellulose (hereinafter, also referred to as "MC") and the like. While the nonionic water-soluble hydroxyalkyl cellulose is not particularly limited, it includes hydroxypropyl cellulose (hereinafter, also referred to as "HPC") and the like. While the nonionic water-soluble hydroxyalkylalkyl cellulose is not particularly limited, it includes hydroxypropyl methylcellulose (hereinafter, also referred to as "HPMC") and the like. While the nonionic water-soluble cellulose ether is not particularly limited in terms of properties such as functional group content and viscosity, each favorable range of such properties is exemplified below taking into consideration compressibility given to the capsule filling composition.

The methoxy group content of MC is preferably in the range between 26.0 wt % and 33.0 wt %, and more preferably between 27.5 wt % and 31.5 wt %. The methoxy group content of MC can be determined according to the measurement method for methylcellulose described in The Japanese Pharmacopoeia, Seventeenth Edition, published by the Japan Ministry of Health, Labour and Welfare, Apr. 1, 2016, Tokyo, Japan, pages 1228-1229.

The hydroxypropoxy group content of HPC is preferably in the range between 53.4 wt % and 77.5 wt %, and more preferably between 60.0 wt % and 70.0 wt %. The hydroxypropoxy group content of HPC can be determined according to the measurement method for hydroxypropyl cellulose described in The Japanese Pharmacopoeia, Seventeenth Edition, published by the Japan Ministry of Health, Labour and Welfare, Apr. 1, 2016, Tokyo, Japan, pages 1033-1034.

The methoxy group content of HPMC is preferably in the range between 16.5 wt % and 30.0 wt %, more preferably between 19.0 wt % and 30.0% wt %, and still more preferably between 19.0 wt % and 29.5 wt %. The hydroxypropoxy group content of HPMC is preferably in the range between 3.0 wt % and 32.0 wt %, more preferably between 3.0 wt % and 12.0 wt %, and still more preferably between 4.0 wt % and 12.0 wt %. The methoxy group content and the hydroxypropoxy group content of HPMC can be determined according to the quantitative method described in the section "Hypromellose" in The Japanese Pharmacopoeia, Seventeenth Edition, published by the Japan Ministry of Health, Labour and Welfare, Apr. 1, 2016, Tokyo, Japan, pages 1038-1039.

The viscosity of the nonionic water-soluble cellulose ether is preferably in the range between 1.0 mPa·s and 150,000 mPa·s, more preferably between 2.0 mPa·s and 120,000 mPa·s, and still more preferably between 2.5 mPa·s and 6,000 mPa·s. The viscosity of the nonionic water-soluble cellulose ether is a value determined according to the method as described in Examples below.

While the ionic water-soluble cellulose ether and its salt are not particularly limited, they include, for example, carboxymethyl cellulose sodium (hereinafter, also referred to as "CMC-Na") and the like. The ionic water-soluble cellulose ether and its salt are not particularly limited in terms of properties such as functional group content and viscosity, each favorable range of such properties is exemplified below taking into consideration compressibility given to the capsule filling composition.

The carboxymethyl group content of CMC-Na is preferably in the range between 22.0 wt % and 32.0 wt %. The carboxymethyl group content of CMC-Na is a value determined according to the method as described in Examples below.

The viscosity of the ionic water-soluble cellulose ether and its salt such as CMC-Na is preferably in the range between 1.0 mPa·s and 2,000 mPa·s, and more preferably between 50 mPa·s and 500 mPa·s. The viscosity of the ionic water-soluble cellulose ether and its salt is a value determined according to the method as described in Examples below.

While the nonionic water-insoluble cellulose ether is not particularly limited, it includes, for example, low substituted hydroxypropyl cellulose (hereinafter also referred to as "L-HPC") and the like. The nonionic water-insoluble cellulose ether is not particularly limited in terms of properties such as functional group content and viscosity, each favorable range of such properties is exemplified taking into consideration compressibility given to the capsule filling composition.

The hydroxypropoxy group content of L-HPC is preferably in the range between 5 wt % and 16 wt %, more preferably between 6 wt % and 15 wt %, and still more preferably between 7 wt % and 14 wt %. The hydroxypropoxy group content of L-HPC can be determined according to the measurement method for low substituted hydroxypropyl cellulose described in The Japanese Pharmacopoeia, Seventeenth Edition, published by the Japan Ministry of Health, Labour and Welfare, Apr. 1, 2016, Tokyo, Japan, page 1035.

The viscosity of nonionic water-insoluble cellulose ether such as L-HPC is preferably in the range between 5 mPa·s and 500 mPa·s, more preferably between 10 mPa·s and 400 mPa·s, and still more preferably between 30 mPa·s and 300 mPa·s. The viscosity of L-HPC is a value determined according to the method as described in Examples below.

While the esterified cellulose ether is not particularly limited, it includes, for example, hydroxypropyl methylcellulose acetate succinate (hereinafter, also referred to as "HPMCAS"), hydroxypropyl methylcellulose phthalate (hereinafter, also referred to as "HPMCP"), and the like. The esterified cellulose ether is not particularly limited in terms of properties such as functional group content and viscosity, each favorable range of such properties is exemplified below taking into consideration compressibility given to the capsule filling composition.

The methoxy group content of HPMCAS is preferably in the range between 12.0 wt % and 28.0 wt %. The hydroxypropoxy group content of HPMCAS is preferably in the range between 4.0 wt % and 23.0 wt %. The acetyl group content of HPMCAS is preferably in the range between 2.0 wt % and 16.0 wt %. The succinyl group content of HPMCAS is preferably in the range between 4.0 wt % and 28.0 wt %. The methoxy group content, the hydroxypropoxy group content, the acetyl group content, and the succinyl group content of HPMCAS can be determined according to the quantitative method described in the section "Hypromellose acetate succinate" in The Japanese Pharmacopoeia, Seventeenth Edition, published by the Japan Ministry of Health, Labour and Welfare, Apr. 1, 2016, Tokyo, Japan, pages 1040-1041.

The methoxy group content of HPMCP is preferably in the range between 16.0 wt % and 26.0 wt %. The hydroxypropoxy group content of HPMCP is preferably in the range between 5.0 wt % and 10.0 wt %. The carboxybenzoyl group content of HPMCP is preferably in the range between 21.0 wt % and 35.0 wt %. The methoxy group content and the hydroxypropoxy group content of HPMCP can be determined according to the quantitative method described in the section "Hypromellose acetate succinate" in The Japanese Pharmacopoeia, Seventeenth Edition, published by the Japan Ministry of Health, Labour and Welfare, Apr. 1, 2016, Tokyo, Japan, pages 1040-1041 and the carboxybenzoyl group content of HPMCP can be determined according to the quantitative method described in the section "Hypromellose phthalate" in The Japanese Pharmacopoeia, Seventeenth Edition, published by the Japan Ministry of Health, Labour and Welfare, Apr. 1, 2016, Tokyo, Japan, pages 1041-1042.

The viscosity of the esterified cellulose ether is the viscosity at 20° C. of a 0.43 wt % sodium hydroxide aqueous solution containing 2 wt % of esterified cellulose ether. The viscosity of the esterified cellulose ether is preferably in the range between 1.0 mPa·s and 100.0 mPa·s. The viscosity of the esterified cellulose ether can be determined according to the method described in the drug monograph "Hypromellose acetate succinate" in The Japanese Pharmacopoeia, Seventeenth Edition, published by the Japan Ministry of Health, Labour and Welfare, Apr. 1, 2016, Tokyo, Japan, pages 1040-1041.

The cellulose ether powder may be used either individually or in combination of two or more of the above-mentioned cellulose ethers in the form of powder. Moreover, the cellulose ether powder may be commercially available or may be produced by known methods.

The content of the cellulose ether powder in the capsule filling composition is not particularly limited, but, taking into consideration compressibility, is preferably in the range between 0.5 wt % and 99.5 wt %, more preferably between 1 wt % and 50 wt %, still more preferably between 3 wt % and 20 wt %, still even more preferably between 3 wt % and 10 wt %.

Additive agents may be contained in the capsule filling composition as required. The additive agents include, but are not limited to, diluting agents, disintegrating agents, binding agents, lubricants, corrigents and flavoring agents.

Examples of the diluting agents include lactose, sucrose, starch, corn starch, pregelatinized starch, saccharose, fructose, maltose, crystalline cellulose, powdered cellulose, maltose, maltitol, erythritol, mannitol, sorbitol, dextrin, maltodextrin, kaolin, calcium carbonate, calcium phosphate, calcium sulfate and the like.

Examples of the disintegrating agents include corn starch, partially pregelatinized starch, sodium carboxymethyl starch, croscarmellose, croscarmellose sodium, crystalline cellulose, crospovidone and the like.

Examples of the binding agents include polyvinylpyrrolidone, starch, polyvinyl alcohol, starch syrup and the like. Examples of the lubricants include magnesium stearate, calcium stearate, talc, sodium stearyl fumarate, sucrose fatty acid ester and the like. Examples of the corrigents include citric acid, tartaric acid and malic acid and the like. Examples of the flavoring agents include menthol, peppermint oil, vanillin and the like.

The additive agents may be used either individually or in combination of two or more of the above-mentioned additive agents. The additive agents may be commercially available or may be produced by known methods.

While the content of the additive agents in the capsule filling composition is not particularly limited, the content may be an amount that does not impair the compressibility of the capsule filling composition given by the cellulose ether powder. For example, the content of the additive agent is preferably in the range between 0 part by weight and 198 parts by weight more preferably between 5 parts by weight and 98.25 parts by weight, and still more preferably between 8 parts by weight and 90 parts by weight relative to 1 part by weight of the cellulose ether powder.

As one specific embodiment of the capsule filling composition, the following capsule filling composition can be included, but the present invention is not limited to these embodiments:

1. a capsule filling composition containing an active ingredient and a cellulose ether powder, wherein the content of the cellulose ether powder is in the range between 0.001 parts by weight and 90 parts by weight relative to 1 part by weight of the active ingredient, and the composition has a property in which total outflow on the evaluation of compressibility is equal to or more than 13.0 times;
2. a capsule filling composition containing an active ingredient and a cellulose ether powder, wherein the content of the cellulose ether powder is in the range between 0.01 parts by weight and 20 parts by weight relative to 1 part by weight of the active ingredient, and the composition has a property in which total outflow on the evaluation of compressibility is equal to or more than 15.0 times;
3. a capsule filling composition containing an active ingredient, a cellulose ether powder and an additive agent, wherein the content of the cellulose ether powder is in the range between 0.001 parts by weight and 90 parts by weight relative to 1 part by weight of the active ingredient, the content of the additive agent is in the range between 10 wt % and 95 wt % in total, and the composition has a property in which total outflow on the evaluation of compressibility is equal to or more than 13.0 times; and
4. a capsule filling composition containing an active ingredient, a cellulose ether powder and an additive agent, wherein the content of the cellulose ether powder is in the range between 0.01 parts by weight and 20 parts by weight relative to 1 part by weight of the active ingredient, the content of the additive agent is in the range between 50 wt % and 90 wt % in total, and the composition has a property in which total outflow on the evaluation of compressibility is equal to or more than 15.0 times.

While the method of producing the capsule filling composition is not particularly limited, and may be a method including a means to make all of components homogeneous. However, in terms of ensuring the quality of capsule formulations by filling the capsule filling composition in a quantitative method, the method of producing the capsule filling composition preferably includes dry blending a raw material containing an active ingredient, a cellulose ether powder and optionally an additive agent to obtain the capsule filling composition containing the active ingredient and the cellulose ether powder.

The means of dry blending is not particularly limited, and can employ known methods of blending all of powdery components maintained in a dried state homogeneously.

<Method of Producing Capsule Formulation, and Capsule Formulation>

The method of producing a capsule formulation according to one embodiment of the present invention includes subjecting a capsule filling composition containing an active ingredient and a cellulose ether powder to a die-compression system powder filling or a funnel system powder filling to prepare a compressed product; and filling the compressed product into a capsule container to obtain the capsule formulation.

The die-compression system powder filling is one of capsule filling methods as generally known, which includes introducing a powder into a molding plate, compressing the powder with a tapping rod to prepare a compressed product, and then scrapping off excess powder followed by transferring the compressed product into a capsule body.

The funnel system powder filling is one of capsule filling methods as generally known, which includes pushing a funnel for filling into a powder layer and compressing the powder to prepare a compressed product, and then transferring the compressed product into a capsule body.

The die-compression system powder filling and the funnel system powder filling can be performed according to conventional methods using a capsule filling machine capable of performing these filling methods. While the capsule filling machine is not particularly limited, it includes, for example, a fully automatic capsule filling machine "LIQFIL super 40" (manufactured by Qualicaps Co., Ltd), an intermittent capsule filling machine "ZANASI 6-12-25-40" (manufactured by IMA S.p.A.), and the like.

Both of the die-compression system powder filling and the funnel system powder filling have a commonality in compressing a capsule filling composition containing an active ingredient and a cellulose ether powder to prepare a compressed product, and then filling the compressed product into a capsule container to obtain a capsule formulation. In other words, the compressed product obtained with the use of the capsule filling composition is prepared as long as the die-compression system powder filling or the funnel system powder filling is employed.

A capsule container consists of a capsule cap and a capsule body. The capsule container used in the method of producing a capsule formulation according to one embodiment of the present invention is not particularly limited in type, material, size, and other properties.

The type of the capsule container is preferably a hard capsule since it allows the compressed product prepared with the use of the capsule filling composition to be easily put in the capsule container. Examples of the material of the capsule container include HPMC hard capsules, gelatin hard capsules, pullulan hard capsules and the like. Examples of the size of the capsule container include No. 00, No. 0, No. 1, No. 2, No. 3, No. 4, No. 5, No. 9 and the like, but any size of capsule containers can be used.

The capsule container may be commercially available or may be manufactured by known methods.

The capsule formulation produced according to the method of producing a capsule formulation according to one embodiment of the present invention contains a capsule filling composition according to one embodiment of the present invention. Another aspect of the present invention is a capsule formulation containing the capsule filling composition according to one embodiment of the present invention.

Further, when a cellulose ether powder having a relatively high viscosity, preferably a nonionic water-soluble cellulose ether powder such as HPMC having a viscosity of the range between 50 mPa·s and 100,000 mPa·s is used as a cellulose ether powder, the resulting capsule formulation can have an excellent sustained release property which suppresses an initial burst.

EXAMPLES

While the present invention will now be described in further detail with reference to Examples and Comparative Examples, the present invention is not limited to these Examples.

<Materials Used>

Koji powder and vitamin $B_2$ were used as an active ingredient. For the koji powder, "multi-grain koji (registered trademark) 50 M" (the compressibility index of 25%; manufactured by YAEGAKI Bio-industry, Inc.) was used. For the vitamin $B_2$, "riboflavin" (the compressibility index of 5%; manufactured by Kyowa Pharma Chemical Co., Ltd.) was used.

Hydroxypropyl methylcellulose (HPMC), methylcellulose (MC), hydroxypropyl cellulose (HPC), sodium carboxy methylcellulose (CMC-Na) and low substituted hydroxypropyl cellulose (L-HPC) produced according to known methods were used for a cellulose ether powder. Physical properties of cellulose ether powders are shown in Table 1.

For lactose, "Pharmatose 100M" (manufactured by DMV) was used. For a capsule container, "size No. 0 HPMC capsule" (manufactured by Hiruherf Research Co. Inc.) was used.

TABLE 1

| Sample name | Cellulose ether powder | Average particle size (μm) | Loose bulk density (g/mL) | Viscosity (mPa · s) | Methoxy group (wt %) | Hydroxypropoxy group (wt %) | Carboxymethyl group (wt %) |
|---|---|---|---|---|---|---|---|
| HPMC-1 | HPMC | 10.2 | 0.12 | 4.0 | 22.8 | 9.2 | — |
| HPMC-2 | HPMC | 68.2 | 0.29 | 4.1 | 22.7 | 9.3 | — |
| HPMC-3 | HPMC | 74.8 | 0.30 | 3800.0 | 22.3 | 9.4 | — |
| MC-1 | MC | 9.4 | 0.11 | 4.0 | 29.4 | — | — |
| MC-2 | MC | 52.1 | 0.28 | 4.0 | 29.4 | — | — |
| HPC | HPC | 107.0 | 0.32 | 4.7 | — | 61.6 | — |
| CMC-Na | CMC-Na | 69.4 | 0.50 | 293.0 | — | — | 28.3 |
| L-HPC | L-HPC | 19.6 | 0.28 | 174.0 | — | 11.0 | — |

<Physical Property Evaluation>

[Average Particle Size]

The average particle size represents a volume-based average particle size measured by a dry laser diffraction method. The average particle size was determined by a 50% cumulative value of a volume-based cumulative particle size distribution curve under the conditions of a dispersion pressure of 1.5 bar and a scattering intensity of the range between 2% and 10% by a dry method with Fraunhofer diffraction theory using a laser diffraction particle size distribution analyzer ("Mastersizer 3000"; manufactured by Malvern Co., Ltd.).

[Loose Bulk Density]

The loose bulk density represents the bulk density of cellulose ether powder in a loosely packed state. The loose bulk density was determined by using a powder property evaluation device "Powder Tester PT-X type" (manufactured by Hosokawa Micron Co., Ltd.) according to the third method of "Measurement method of bulk density and tap density" in The Japanese Pharmacopoeia, Seventeenth Edition.

[Viscosity]

1. HPMC, MC and HPC

An amount equivalent to 6 g of the dry matter of HPMC, MC or HPC calculated on the dried basis was accurately weighed in a wide-mouth bottle (with a diameter of 65 mm; height of 120 mm; volume of 350 ml), and hot water at 98° C. was added to the wide-mouth bottle so as to be 2% by weight. After a lid was put on the wide-mouth bottle, the mixture was stirred with a stirrer at between 350 rpm and 500 rpm for 20 minutes until a homogeneous dispersion was obtained. Subsequently, the cellulose ether was dissolved by stirring the dispersion in a water bath at between 0° C. and 5° C. for 40 minutes, resulting in a 2 wt % aqueous solution of cellulose ether as a sample solution.

The viscosity at 20° C. of the 2 wt % aqueous solution of cellulose ether, if its viscosity was equal to or more than 600 mPa·s, was determined by using a single cylindrical rotational viscometer according to the rotational viscometer method in the General Tests "Viscosity Determination" in The Japanese Pharmacopoeia, Seventeenth Edition, published by the Japan Ministry of Health, Labour and Welfare, Apr. 1, 2016, Tokyo, Japan, pages 71-74. On the other hand, the viscosity at 20° C. of the 2 wt % aqueous solution of cellulose ether, if its viscosity was less than 600 mPa·s, was determined by using an Ubbelohde-type viscometer according to the capillary viscometer method in the General Tests "Viscosity Determination" in The Japanese Pharmacopoeia, Seventeenth Edition, published by the Japan Ministry of Health, Labour and Welfare, Apr. 1, 2016, Tokyo, Japan, pages 71-74.

2. CMC-Na

CMC-Na (about 2.2 g) was placed in a 300 ml-volume Erlenmeyer flask with a stopper equipped, and weighed precisely. Water was added to the flask in an amount calculated by the following formula: sample (g)×(99−water content (wt %))", and the mixture was left to stand for 12 hours and further mixed for 5 minutes to prepare a 1 wt % aqueous solution of CMC-Na.

The viscosity at 25° C. of the 1 wt % aqueous solution of CMC-Na was determined by using a BM type viscometer (single cylindrical rotational viscometer) according to Japanese Industrial Standard (JIS) JIS Z8803 (published by the Japanese Standards Association, 2011, Tokyo, Japan, 54 pages).

3. L-HPC

An amount equivalent to 15 g of the dry matter of L-HPC calculated on the dried basis was accurately weighted in a wide-mouth bottle (with a diameter of 65 mm; a height of 120 mm; a volume of 350 ml), and purified water at 20° C. was added to the wide-mouth bottle so as to be 5% by weight. After a lid was put on the wide-mouthed bottle, the mixture was stirred with a stirrer at between 350 rpm and 500 rpm for 20 minutes until a homogeneous dispersion was obtained, resulting in a 5 wt % aqueous dispersion of water-insoluble cellulose ether as a sample solution.

The viscosity at 20° C. of the 5 wt % aqueous dispersion of L-HPC was determined by using a single cylindrical rotational viscometer according to the single rotational viscometer in the General Tests "Viscosity Determination" in The Japanese Pharmacopoeia, Seventeenth Edition, published by the Japan Ministry of Health, Labour and Welfare, Apr. 1, 2016, Tokyo, Japan, pages 71-74.

[The Contents of Methoxy Group, Hydroxypropoxy Group and Carboxymethyl Group]

The methoxy group contents of HPMC and MC were determined according to the quantitative method described in the sections "Hypromellose" and "Methylcellulose" in The Japanese Pharmacopoeia, Seventeenth Edition, published by the Japan Ministry of Health, Labour and Welfare, Apr. 1, 2016, Tokyo, Japan, pages 1038-1039 and 1228-1229, respectively. The hydroxypropoxy group contents of HPMC, HPC and L-HPC were determined according to the quantitative method described in the sections "Hypromellose," "Hydroxypropyl cellulose," and "Low substituted hydroxypropyl cellulose" in The Japanese Pharmacopoeia, Seventeenth Edition, published by the Japan Ministry of Health, Labour and Welfare, Apr. 1, 2016, Tokyo, Japan, pages 1038-1039, 1033-1034, and 1035, respectively.

The carboxymethyl group content of CMC-Na was calculated from the degree of substitution of CMC-Na according to the following formula:

$$\text{The carboxymethyl group content of CMC-Na} = (81 \times 100 \times CM)/(162 + 64 \times CM)$$

CM: degree of substitution of CMC-Na
162: molecular weight of glucose
81: molecular weight of CH$_2$COONa
64: increased molecular weight of CH$_2$COONa The degree of substitution in CMC-Na was determined according to the following method.

First, 0.5 g to 0.7 g of a CMC-Na sample (anhydrous) was precisely weighed, wrapped in a filter paper, and ashed in a magnetic crucible. Next, the ashed CMC-Na was cooled, and then transferred into a 500 mL-volume beaker. Water (250 mL) and 0.05 M sulfuric acid (35 mL) were added to the beaker, and then the solution in the beaker was boiled for 30 minutes. After cooling the boiled solution, a phenolphthalein indicator was added to the solution, and excess sulfuric acid was back titrated with 0.1 M potassium hydroxide and the degree of substitution in CMC-Na was calculated according to the following formula:

$$\text{Degree of substitution in CMC-Na}(CM) = (162 \times A)/(10000 - 80 \times A)$$

162: molecular weight of glucose
80: molecular weight of CH$_2$COONa—H

"A" in the above formula stands for the amount (mL) of 0.05 M sulfuric acid consumed by alkali in 1 g of a CMC-Na sample, and was calculated according to the following formula:

$$A = ((a \times f - b \times f1)/\text{CMC-Na sample (anhydride) (g)}) - \text{alkalinity (or+acidity)}$$

a: amount of 0.05 M sulfuric acid used (mL)
f: titer of 0.05 M sulfuric acid
b: amount of 0.1 M potassium hydroxide titrated (mL)
f1: titer of 0.1 M potassium hydroxide Further, the alkalinity (or acidity) was determined by the following method.

A CMC-Na sample (anhydrous) (1 g) was precisely weighted in a 300 mL flask, and 200 mL of water was added to the flask and the CMC-Na sample was dissolved. Five milliliters of 0.05 M sulfuric acid was added to the obtained CMC-Na solution, and the solution was boiled for 10 minutes and then cooled. A phenolphthalein indicator was added to the cooled solution and titrated with 0.1 M potassium hydroxide (S mL). A blank test was performed concurrently (B mL). Alkalinity (or acidity) was calculated according to the following formula:

Alkalinity=((B−S)×f2)/CMC-Na sample (anhydrous)
(g) f2: titer of 0.1 M potassium hydroxide When the value of "(B−S)×f2" is a negative value, the term "alkalinity" represents "acidity."

[Compressibility Index]

The active ingredient weighing 2,000 mg was introduced into a polycarbonate tube (a hollow cylindrical form with an inner diameter of 12.5 mm and a height of 52.0 mm; "polycarbonate spacer (hollow) CPC (CPC-1252); manufactured by Hirosugi Keiki Co., Ltd.) which was left to stand on a stainless steel bat. Next, by using a tension and compression testing machine ("SDT—503 NB"; manufactured by Imada Seisakusho Co., Ltd.), the active ingredient within the polycarbonate tube was compressed by a cylindrical tool having a contact surface of 11.28 mmΦ in diameter to prepare a compressed product (compression condition; speed: 100 mm/min., load: 0.5 N, load maintaining time: 1 sec.). The weight of the polycarbonate tube containing the compressed product of the active ingredient was weighted as a weight before test.

Then, the polycarbonate tube filled with the compressed product of the active ingredient was placed to leave to stand on mesh sieves (test sieves JIS Z 8801; φ 200 mm×45 mmH, with aperture of 1.4 mm; manufactured by Tokyo Screen Co., Ltd.) with a saucer combined, and the polycarbonate tube was pinched with fingers of human being and then was lifted to a height of 1 cm in the vertical direction.

The lifted polycarbonate tube was released from the fingers, and dropped down. After repeating this procedure three times, the remaining weight of the polycarbonate tube containing the compressed product of the active ingredient was measured as a weight after test.

The amount of powder flowing out from the polycarbonate tube was determined by subtracting the weight after test from the weight before test. Furthermore, the remaining weight of the compressed product of the active ingredient was determined by subtracting the amount of powder flowing out from the polycarbonate tube from the weight before test. The number of tests was set to 5, and the compressibility index of the active ingredient was calculated by dividing the average value of the remaining weight of the compressed product of the active ingredient by the introduced weight of the active ingredient (2000 mg).

[Compressibility]

A polycarbonate tube containing the compressed product of the capsule filling composition was prepared and weighted as described in [Compressibility index] above, except that the capsule filling compositions described below were used instead of the active ingredient.

The polycarbonate tube containing the compressed product of the capsule filling composition was dropped down as described in [Compressibility index] above, and the remaining weight of the polycarbonate tube containing the compressed product of the active ingredient was measured after the third dropping and the fifth dropping. The amount of powder flowing out from the polycarbonate tube was determined by subtracting the weight after dropping from the weight before dropping. Moreover, the number of droppings required until the total amount of the capsule filling composition can flow out from the polycarbonate tube was counted. The number of tests was set to 5, and the average value was used for evaluation of compressibility.

[Dissolution Amount]

Dissolution amounts of capsule formulations described below were determined with the use of a dissolution tester ("NTR—6400 A"; manufactured by Toyama Sangyo Co., Ltd.) by carrying out the dissolution test according to "Dissolution Test" (37° C., paddle method, using of a sinker, 50 rpm/minute, 900 mL of purified water for solvent) described in The Japanese Pharmacopoeia, Seventeenth Edition, published by the Japan Ministry of Health, Labour and Welfare, Apr. 1, 2016, Tokyo, Japan, pages 157-161.

<Production of Capsule Filling Composition and Compressed Product>

Example 1

Using HPMC-1 described in Table 1 as the cellulose ether powder, koji powder as the active ingredient and HPMC-1 as the cellulose ether powder were weighed so as to become each content shown in Table 2, and were subjected to dry blending to produce a capsule filling composition.

Using the produced capsule filling composition, a compressed product was produced by compressing the capsule filling composition within the polycarbonate tube according to the method described in [Compressibility] described above.

Examples 2 to 9 and Comparative Example 1

In the same method as in Example 1, using the cellulose ether powder shown in Table 1, the active ingredient and the cellulose ether powder were weighed so as to become each content shown in Table 2, and were subjected to dry blending to produce a capsule filling composition and a compressed product. In Comparative Example 1, however, any cellulose ether powder was not used.

Example 10 and Comparative Example 2

According to the same method as in Example 1, using HPMC-3 shown in Table 1, vitamin $B_2$ as the active ingredient, the cellulose ether powder and lactose as the diluting agent were weighted so as to become each content shown in Table 3, and blended to produce a capsule filling composition and a compressed product.

In Comparative Example 2, any cellulose ether powder was not used.

<Production of Capsule Formulation>

Example 10 and Comparative Example 2

Each of 450 mg of capsule filling composition of Example 10 and Comparative Example 2 was weighed, and then each composition was introduced in a die having a diameter of 7 mm (IPT standard; manufactured by Kikusui Seisakusho Ltd.) that was left to stand on a stainless steel bat. Using a tension and compression testing machine ("SDT—503 NB"; manufactured by Imada Seisakusho Co., Ltd.), the capsule filling composition in the die was compressed with a load of 0.19 N using a punch having a diameter of 7 mm and 10 mmR
(IPT standard; manufactured by Kikusui Seisakusho Co., Ltd.) to prepare a compressed product.

Next, the compressed product was extruded from the die and filled into a separated hard capsule body, and then a capsule cap was bonded to the capsule body to produce a capsule formulation.

<Evaluation of Compressed Product>

Table 2 shows the evaluation results of compressibility according to Examples 1 to 9 and Comparative Example 1. From Table 2, it was found that the use of the cellulose ether powder improved the compressibility of the active ingredient. Accordingly, it is expected that in the production process of capsule formulations, the use of the cellulose ether powder could prevent the capsule formulations from having weight variations due to outflows of the active ingredient caused by mechanical vibrations during capsule filling, resulting in the stable production of capsule formulations with a constant weight.

From Examples 1 and 2, it was also found that the improved compressibility was more exerted when the content of the cellulose ether powder increased.

Furthermore, from Examples 1 and 3, it was found that the smaller the average particle size of the cellulose ether powder was, the more the compressibility was improved.

Besides, from Examples 1 and 3, it was found that the lower the viscosity of the cellulose ether powder was, the more the compressibility was improved.

In addition, from Examples 5 to 9, it was found that the improved compressibility was exhibited even when the various types of cellulose ether powder were employed.

From Example 10 and Comparative Example 2, it was confirmed that the favorable compressibility was exhibited even when containing the different active ingredient from those of Examples 1 to 9 and further containing the diluting agent.

<Evaluation of Capsule Formulation>

Table 3 shows the dissolution rates of vitamin $B_2$ 0 hour, 0.5 hours, 1 hour, 2 hours, 3 hours, 4 hours and 5 hours on dissolution test.

From Example 10 and Comparative Example 2, it was found that the use of the high viscosity cellulose ether powder could prevent the capsule formulations from causing an initial burst, and theretofore achieved a favorably sustained release property of the capsule formulations.

TABLE 2

| Capsule filling composition | | | | Compressibility evaluation | | Total |
|---|---|---|---|---|---|---|
| Active ingredient | | Cellulose ether powder | | Third time | Fifth time | outflows Number |
| Type | wt % | Type | wt % | mg | mg | of times |
| Example 1 | Koji | 97 | HPMC-1 | 3 | 289.9 | 521.5 | 22.6 |
| Example 2 | Koji | 95 | HPMC-1 | 5 | 271.7 | 473.4 | 24.2 |
| Example 3 | Koji | 97 | HPMC-2 | 3 | 312.4 | 565.1 | 20.3 |
| Example 4 | Koji | 95 | HPMC-3 | 5 | 407.0 | 581.5 | 19.9 |
| Example 5 | Koji | 97 | MC-1 | 3 | 377.3 | 634.7 | 15.5 |
| Example 6 | Koji | 95 | MC-2 | 5 | 299.9 | 575.3 | 23.1 |
| Example 7 | Koji | 95 | HPC | 5 | 334.6 | 581.2 | 17.3 |
| Example 8 | Koji | 95 | CMC-Na | 5 | 360.4 | 624.9 | 16.0 |
| Example 9 | Koji | 95 | L-HPC | 5 | 403.4 | 570.1 | 15.7 |
| Comp Ex 1 | Koji | 100 | — | 0 | 499.0 | 765.8 | 12.2 |

TABLE 3

| Capsule filling composition | | | | | | Compressibility evaluation | | Total | | | | | | | |
|---|---|---|---|---|---|---|---|---|---|---|---|---|---|---|---|
| Active ingredient | | Cellulose ether powder | | Excipient | | Third time | Fifth time | outflows Number | Dissolution amount (%) | | | | | | |
| Type | wt % | Type | wt % | Type | wt % | mg | mg | of times | 0 h | 0.5 h | 1 h | 2 h | 3 h | 4 h | 5 h |
| Example 10 | Vitamin $B_2$ | 1 | HPMC-3 | 10 | Lactose | 89 | 315.54 | 465.55 | 27.3 | 0 | 5 | 20 | 56 | 83 | 97 | 99 |
| Comp. Ex. 2 | Vitamin $B_2$ | 1 | — | 0 | Lactose | 99 | 523.42 | 818.13 | 9.6 | 0 | 100 | 100 | 100 | 100 | 100 | 100 |

INDUSTRIAL APPLICABILITY

The present invention can be used for stably producing capsule formulations containing a constant weight of components, in which weight variations are suppressed.

I claim:

1. A method of producing a capsule formulation, comprising dry blending a raw material comprising an active ingredient and a cellulose ether powder to obtain a capsule filling composition comprising the active ingredient and the cellulose ether powder; subjecting the capsule filling composition to a funnel system powder filling or a die-compression system powder filling to prepare a compressed product; and filling a capsule container with the compressed product to obtain the capsule formulation, wherein the funnel system powder filling comprises pushing a funnel for filling into a powder layer and compressing the powder to prepare a compressed product, and then transferring the compressed product into a capsule body;

the die-compression system powder filling comprises introducing a powder into a molding plate, compressing the powder with a tapping rod to prepare a compressed product, and then scraping off excess powder followed by transferring the compressed product into a capsule body; and wherein the capsule formulation comprises a capsule filling composition containing an active ingredient, a cellulose ether powder and an additive agent, wherein the content of the cellulose ether powder is in the range between 0.01 parts by weight and 20 parts by weight relative to 1 part by weight of the active ingredient.

2. The method according to claim 1, wherein the cellulose ether powder is a cellulose ether powder having an average particle size equal to or less than 150 μm, wherein the average particle size is 50% cumulative value of volume-based cumulative particle size distribution curve according to dry laser diffraction method.

3. The method according to claim 1, wherein the cellulose ether powder is a cellulose ether powder having a loose bulk density equal to or less than 0.55 g/mL.

4. The method according to claim 1, wherein the cellulose ether powder is at least one cellulose ether powder selected from the group consisting of a nonionic water-soluble cellulose ether, an ionic water-soluble cellulose ether and salt thereof, a nonionic water-insoluble cellulose ether, and an esterified cellulose ether.

5. The method according to claim 4, wherein the nonionic water-soluble cellulose ether is at least one nonionic water-soluble cellulose ether selected from the group consisting of nonionic water-soluble alkyl cellulose, nonionic water-soluble hydroxyalkyl cellulose and nonionic water-soluble hydroxyalkyl alkylcellulose.

6. The method according to claim 1, wherein the compressed product is a compressed product obtained by compressing the capsule filling composition with a load of 0.19 N to 0.5 N.

* * * * *